United States Patent
Rohl et al.

(10) Patent No.: US 10,874,388 B2
(45) Date of Patent: Dec. 29, 2020

(54) CONNECTED ANCHOR DELIVERY SYSTEMS AND METHODS FOR VALVE REPAIR

(71) Applicants: Boston Scientific Scimed, Inc., Maple Grove, MN (US); Mayo Foundation for Medical Education and Research, Rochester, MN (US)

(72) Inventors: James P. Rohl, Prescott, WI (US); Katherine L. Baldwin, Minneapolis, MN (US); James K. Cawthra, Jr., Ramsey, MN (US); Dennis B. Werner, Big Lake, MN (US); William C. Stoffregen, Lake Elmo, MN (US); Daniel Shuey, Pine City, MN (US); Leo H. Ihlberg, Espoo (FI); Richard C. Daly, Rochester, MN (US); Joseph A. Dearani, Rochester, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/122,608

(22) Filed: Sep. 5, 2018

(65) Prior Publication Data
US 2019/0159770 A1    May 30, 2019

Related U.S. Application Data

(60) Provisional application No. 62/593,165, filed on Nov. 30, 2017.

(51) Int. Cl.
*A61B 17/00* (2006.01)
*A61B 17/56* (2006.01)
(Continued)

(52) U.S. Cl.
CPC .... *A61B 17/0401* (2013.01); *A61B 17/00234* (2013.01); *A61B 17/0469* (2013.01);
(Continued)

(58) Field of Classification Search
CPC .......... A61B 17/0401; A61B 17/00234; A61B 17/0469; A61B 17/064; A61B 17/0644;
(Continued)

(56) References Cited

U.S. PATENT DOCUMENTS

| 5,634,936 A | 6/1997 | Linden et al. |
| 5,853,422 A | 12/1998 | Huebsch et al. |

(Continued)

FOREIGN PATENT DOCUMENTS

| WO | 0200099 A2 | 1/2002 | |
| WO | WO-0200099 A2 * | 1/2002 | ......... A61B 17/0644 |

(Continued)

OTHER PUBLICATIONS

International Search Report and Written Opinion for application No. PCT/US2018/049584, dated Dec. 3, 2018, 11 pages.

(Continued)

*Primary Examiner* — Pedro Philogene

(57) ABSTRACT

Anchor delivery systems and methods for repairing a valve inside a body, such as an atrioventricular valve, may include an anchor delivery device including a sheath for at least partially retaining an anchor in a collapsed form. The anchor delivery device may be configured to deliver the anchor to the atrioventricular valve. The anchor and an adjacent anchor may be connectable to each other in an expanded form, to link a series of anchors implanted at least partially around the atrioventricular valve. In some embodiments, the anchors may be connectable by a connecting member, such as a pledget, or a material disposable on a bulb of the anchor. In other embodiments, a bulb of the anchor and a bulb of the
(Continued)

adjacent anchor may be configured to be directly interlocked.

19 Claims, 20 Drawing Sheets

(51) Int. Cl.
*A61B 17/04* (2006.01)
*A61F 2/24* (2006.01)

(52) U.S. Cl.
CPC .......... *A61F 2/2442* (2013.01); *A61F 2/2466* (2013.01); *A61B 2017/00243* (2013.01); *A61B 2017/00783* (2013.01); *A61B 2017/00867* (2013.01); *A61B 2017/0409* (2013.01); *A61B 2017/0464* (2013.01); *A61F 2250/006* (2013.01)

(58) Field of Classification Search
CPC ............ A61B 17/0684; A61B 17/0466; A61B 2017/00243; A61B 2017/00783; A61B 2017/00867; A61B 2017/0409; A61B 2017/0464; A61B 2017/00004; A61B 2017/0414; A61B 2017/0496; A61B 2017/0641; A61F 2/2442; A61F 2/2466; A61F 2/2445; A61F 2250/006
USPC ......... 606/60, 150, 153, 216, 221, 219, 139, 606/144, 148, 213–215, 217–220, 232, 606/123, 157; 128/898; 604/171, 604/174–176
See application file for complete search history.

(56) References Cited

U.S. PATENT DOCUMENTS

| | | | |
|---|---|---|---|
| 5,961,539 A * | 10/1999 | Northrup, III | A61B 17/0401 606/148 |
| 6,024,756 A | 2/2000 | Huebsch et al. | |
| 6,117,159 A | 9/2000 | Huebsch et al. | |
| 6,270,515 B1 | 8/2001 | Linden et al. | |
| 6,312,446 B1 | 11/2001 | Huebsch et al. | |
| 6,626,930 B1 * | 9/2003 | Allen | A61B 17/0401 606/213 |
| 7,695,425 B2 * | 4/2010 | Schweich | A61B 17/00234 600/16 |
| 8,961,594 B2 | 2/2015 | Maisano et al. | |
| 8,961,596 B2 | 2/2015 | Maisano et al. | |
| 9,241,702 B2 | 1/2016 | Maisano et al. | |
| 9,713,465 B1 * | 7/2017 | Nakao | A61B 17/0469 |
| 2003/0199974 A1 | 10/2003 | Lee et al. | |
| 2005/0250986 A1 | 11/2005 | Rothe et al. | |
| 2005/0250988 A1 | 11/2005 | Ewers et al. | |
| 2007/0073337 A1 | 3/2007 | Abbott et al. | |
| 2007/0112425 A1 | 5/2007 | Schaller et al. | |
| 2012/0296349 A1 | 11/2012 | Smith et al. | |
| 2015/0045879 A1 | 2/2015 | Longoria et al. | |
| 2018/0110563 A1 | 4/2018 | Rohl et al. | |
| 2018/0214269 A1 * | 8/2018 | Wilson | A61F 2/2466 |

FOREIGN PATENT DOCUMENTS

| | | |
|---|---|---|
| WO | 2006039199 A2 | 4/2006 |
| WO | 2007009021 A2 | 1/2007 |
| WO | 2007070753 A2 | 6/2007 |

OTHER PUBLICATIONS

Nicotera, P., and Orrenius, S., "The role of calcium in apoptosis", Cell Calcium, 23(2-3): 173-180 (1998).

Frandsen, S.K., et al., "Calcium Electroporation: Evidence for Differential Effects in Normal and Malignant Cell Lines, Evaluated in a 3D Spheroid Model", PloS One pp. 1-11 (2015).

Mattson, M.P., and Chan, S.L., "Calcium orchestrates apoptosis", Nature Cell Biology 5(12):1041-1043 (2003).

International Search Report and Written Opinion, Application No. PCT/US2018/049584, dated Dec. 3, 2018, 10 pages.

* cited by examiner

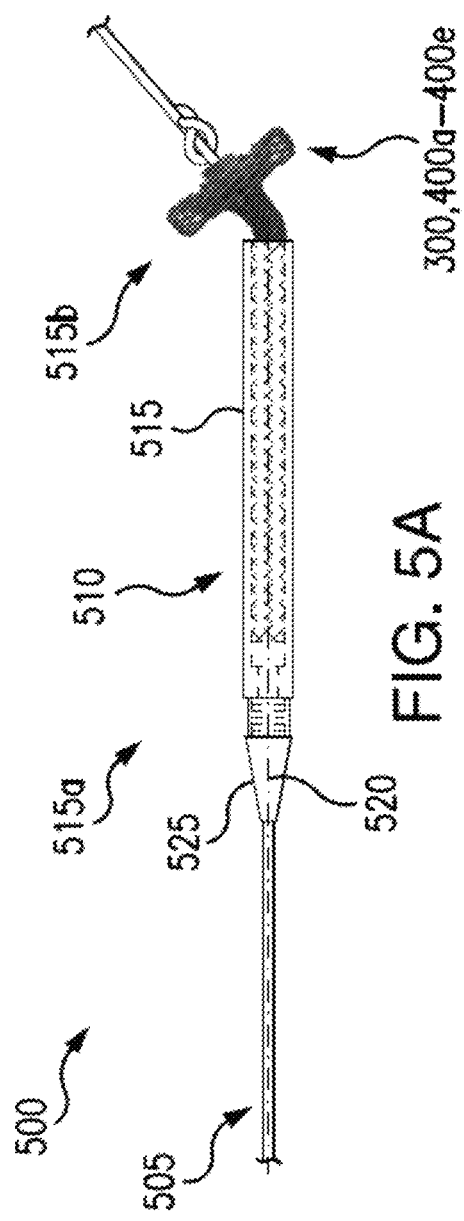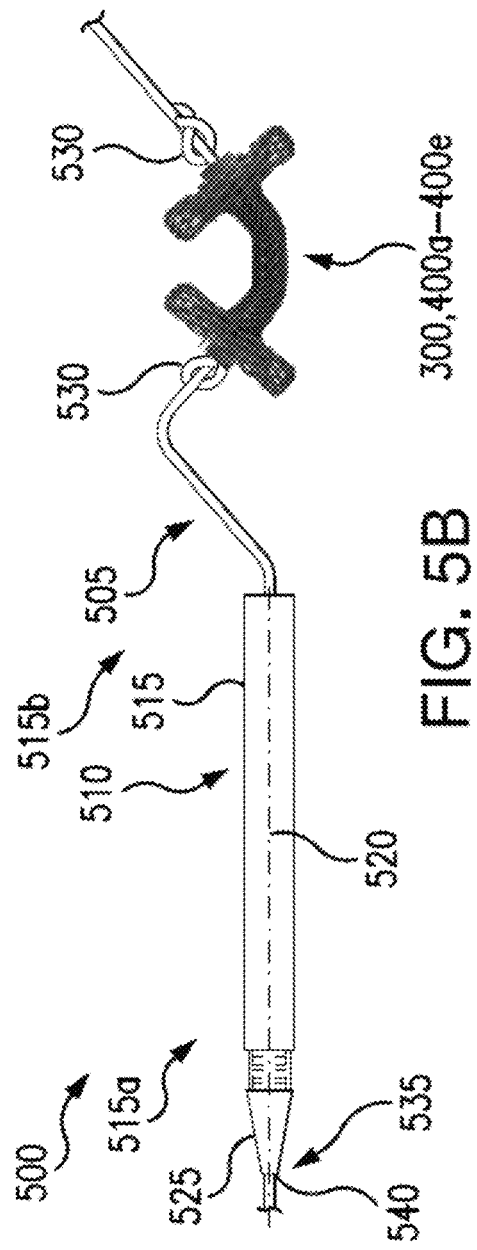

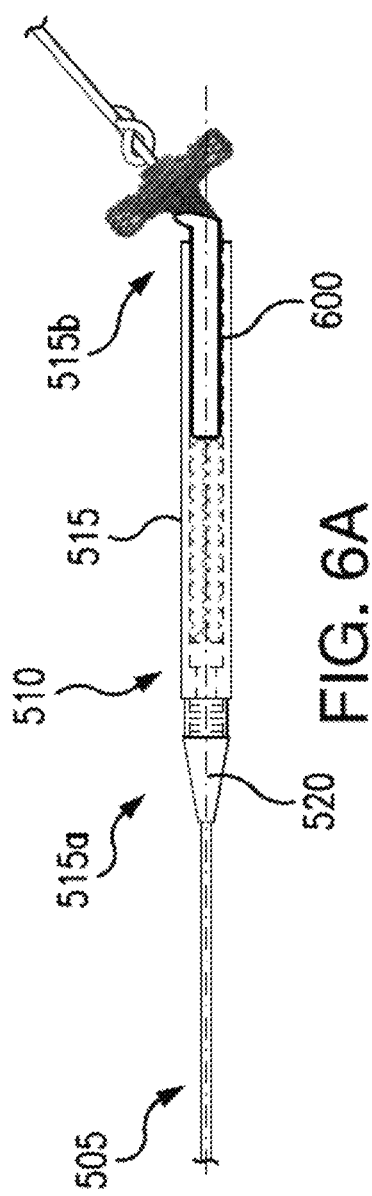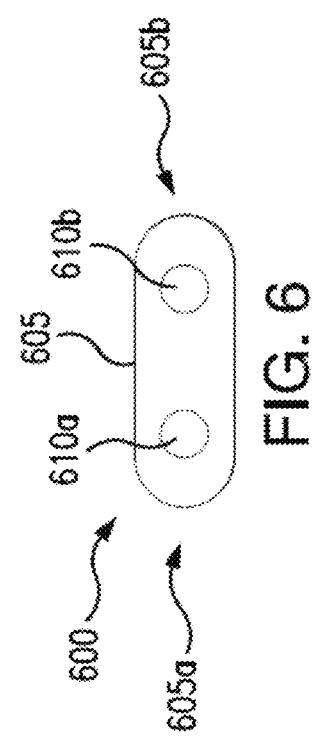

CONNECTED ANCHOR DELIVERY SYSTEMS AND METHODS FOR VALVE REPAIR

CROSS-REFERENCE TO RELATED APPLICATIONS

This application is a non-provisional application of, and claims the benefit of priority to, U.S. Provisional Application Ser. No. 62/593,165, filed Nov. 30, 2017, entitled "Connected Anchor Delivery Systems and Methods for Valve Repair," the entirety of which application is expressly incorporated by reference herein.

FIELD

The present disclosure relates generally to systems and methods for valve repair, more particularly, anchor delivery systems and methods for annular reduction of an atrioventricular valve, such as the mitral and tricuspid valves.

BACKGROUND

A valve in the body may have damaged or weakened annular tissue that requires repair to help improve the function of the valve. As an example, atrioventricular valves of the heart include a mitral, or bicuspid, valve, and a tricuspid valve. For example, FIGS. 1A and 1B illustrate a tricuspid valve in various enlarged states, e.g., FIG. 1B shows a tricuspid valve opening greater than a tricuspid valve illustrated in FIG. 1A. FIG. 2A shows a mitral valve 200 in a closed, e.g., a normal, position, and FIG. 2B shows a mitral valve 205 in an enlarged position. The mitral valve 200, 205 is a dual flap valve having an anterior leaflet 220 and a posterior leaflet 225 surrounded by annular tissue, e.g., an annulus 210, 215 disposed between the left atrium and the left ventricle of the heart, and the tricuspid valve 100, 105 has three leaflets (e.g., anterior 120, posterior 125, and septal 130) surrounded by an annulus 110, 115 disposed between the right atrium and the right ventricle of the heart. When the mitral and tricuspid valves function properly, the valves act to prevent backflow of blood from the ventricles to the atria during systole. When a patient has a disorder of the heart, mitral regurgitation (MR) and/or tricuspid regurgitation (TR) may occur where blood leaks backward through the valve when the respective ventricle contracts. For example, an enlarged ventricle may affect the respective valve in that it will not fully close, allowing leakage to occur. This mitral annular dilation and/or tricuspid annular dilation results in mitral regurgitation and/or tricuspid regurgitation.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, an anchor delivery system for repairing an atrioventricular valve may include an anchor delivery device including a sheath for at least partially retaining an anchor in a collapsed form, wherein the anchor delivery device may be configured to deliver the anchor to the atrioventricular valve. The anchor and an adjacent anchor may be connectable to each other in an expanded form, to link a series of anchors implanted around the atrioventricular valve.

According to an exemplary embodiment of the present disclosure, a method for repairing an atrioventricular valve may include (a) piercing an annulus tissue at a first location by a needle to thread a suture through the annulus tissue to a second location. The suture may extend through an anchor delivery device at least partially housing a first anchor, and the first anchor may be connected to the suture for threading through the annulus tissue such that a first bulb of the first anchor may be deployed at the first location of the annulus tissue. The method may further include (b) extending the anchor delivery device at least partially through the second location of the annulus tissue; (c) deploying a second bulb of the first anchor at the second location by deploying the anchor from the anchor delivery device, wherein the first anchor may contact the annulus tissue; implanting a second anchor according to steps (a)-(c); and connecting the first anchor and the second anchor.

In various of the foregoing and other embodiments of the present disclosure, the systems and methods may include that the anchor is attached to a suture, and the suture may extend through the anchor delivery device for delivery through annulus tissue of the atrioventricular valve. A needle may be configured to pierce the annulus tissue, and the needle may be attached to the suture to pull at least the anchor delivery device or the anchor, or both, through the annulus tissue of the atrioventricular valve.

In various of the foregoing and other embodiments of the present disclosure, the systems and methods may include that the anchor and the adjacent anchor in the expanded form comprise a bulb at either end, and wherein a bulb of the anchor is connectable to a bulb of the adjacent anchor by a connecting member. The connecting member may be a pledget, such that the anchor is extendable through a first opening of the pledget and the adjacent anchor is extendable through a second opening of the pledget. The connecting member may be a material disposable on the bulbs of the anchors such that the material interlocks the bulbs of the anchor and adjacent anchor. The connecting member may be formed of an electro spun nanofiber material. The anchor and the adjacent anchor may be connectable to promote tissue growth. The bulbs on the anchor and the adjacent anchor may be an elliptical shape.

In various of the foregoing and other embodiments of the present disclosure, the systems and methods may include that at least a portion of the anchor retained in the sheath is expandable after deployment in annulus tissue of the atrioventricular valve. The suture may be internal to the anchor, such that as the suture is pulled the anchor may be held in tension in the collapsed form. The suture may be looped externally through the anchor, such that as the suture is pulled the anchor may be held in tension in the collapsed form.

In various of the foregoing and other embodiments of the present disclosure, the systems and methods may include that a bulb of the anchor and a bulb of the adjacent anchor may be configured to be directly interlocked together. The anchor and the adjacent anchor may be configured to be directly interlocked by threading at least a portion of the anchor delivery device through the bulb of the anchor, such that the adjacent anchor may be interlocked with the anchor when deployed.

In various of the foregoing and other embodiments of the present disclosure, the systems and methods may include that the pledget is configured to collapse within the anchor delivery device, such that for delivering a first anchor to annulus tissue, the pledget may be deployable for connecting the first anchor to a second anchor.

In various of the foregoing and other embodiments of the present disclosure, the systems and methods may include that the first anchor and the second anchor may be connected by a connecting member. The connecting member may be a pledget. The connecting member may be a material disposed on the first bulb and the second bulb of the first and second anchors. The first anchor and the second anchor may be interlocked to connect the first or second bulb of the first anchor to the first or second bulb of the second anchor.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 5A-5B illustrate an exemplary embodiment of a delivery device with an anchor in accordance with the present disclosure;

FIG. 6 illustrates an exemplary embodiment of a pledget in accordance with the present disclosure;

FIG. 6A illustrates an exemplary embodiment of a pledget and an anchor in a delivery device in accordance with the present disclosure;

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

While emphasis and discussion is focused in the present disclosure on embodiments of a device, systems, and anchor configurations to reduce annular tissue around mitral and/or tricuspid valves, the breadth of the disclosure is intended to encompass such devices, systems, and methods to deliver various configurations of anchors for anchoring tissue to reduce and repair valves generally in various parts of a human or animal body. In contrast to the anchors of the present disclosure, an annuloplasty ring or band may be placed around a valve and held in place by sutures. The annuloplasty ring or band may create one or more tissue plications, or folds in the annular tissue, to reduce the perimeter of the annulus and to induce leaflet coaptation. Existing repairs for mitral and tricuspid valves by sutures may be disadvantageous because the sutures may split or tear over time, requiring a patient to undergo further surgical repairs. Additionally, an improper band or ring size may increase the likelihood of tearing thereby requiring surgical repairs sooner than desired. When the annuloplasty ring or band dislodges, the valve may once again leak blood back into the respective atrium, causing the patient discomfort and weakness.

Figure 1A:
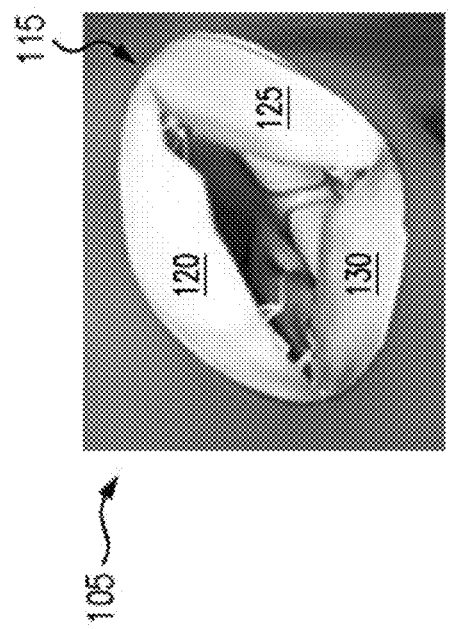
FIGS. 1A-1B illustrate a tricuspid valve in enlarged states.
Figure 1B:
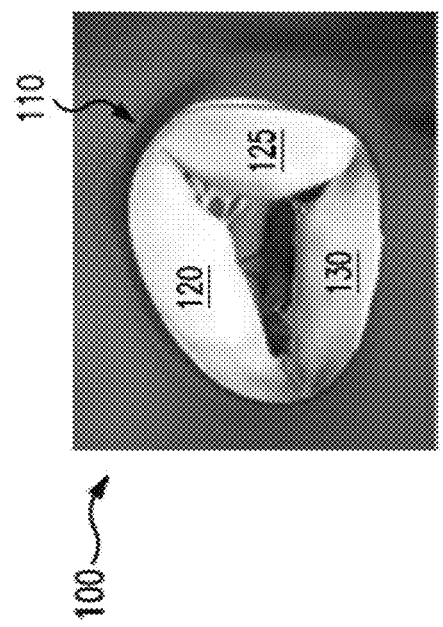
Figure 2B:
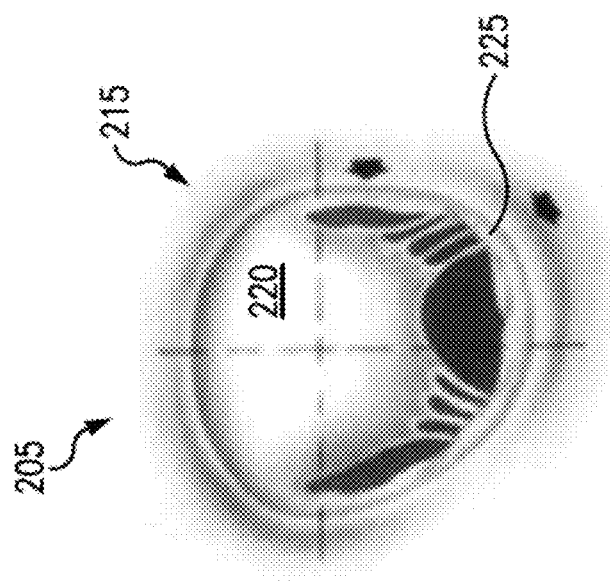
FIGS. 2A-2B illustrate a bicuspid valve in a closed state and an enlarged state.
Figure 2A:
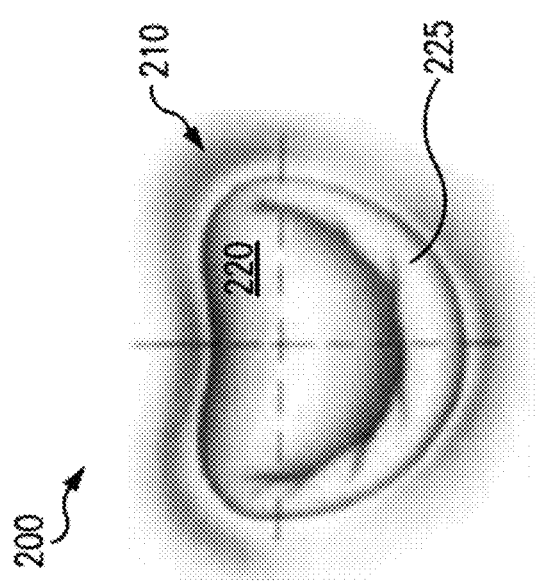
Figure 3B:
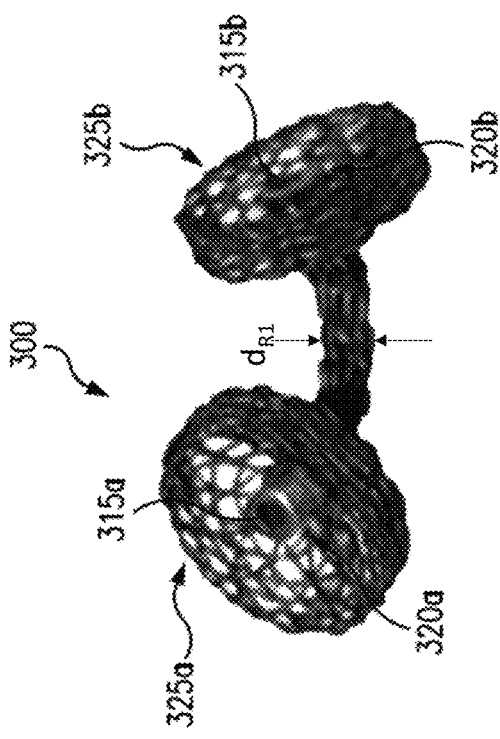
FIGS. 3A-3C illustrate an exemplary embodiment of an anchor in accordance with the present disclosure.
Figure 3C:
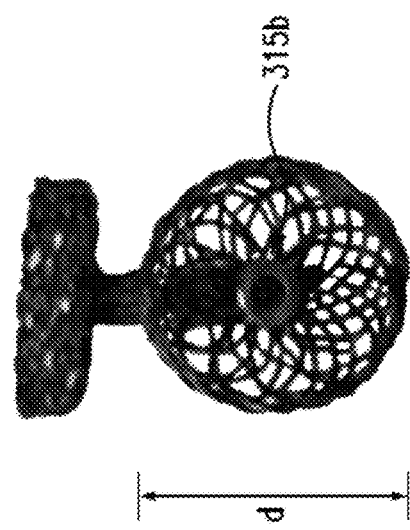
Figure 3A:
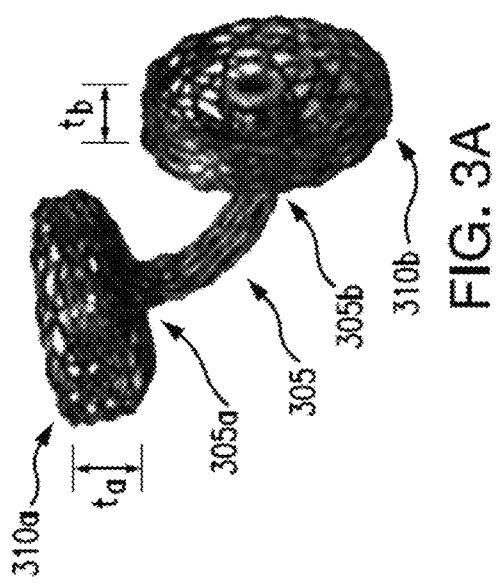

The systems and methods described herein are intended to overcome the disadvantages in existing valve repair devices and processes by delivering one or more anchors to the annular tissue around the valve, thereby allowing for a partial or full reduction so that the valve may close. Referring now to FIGS. 3A-3C, an exemplary embodiment of a mitral and/or tricuspid annular reduction anchor (MARA/TARA) 300 in accordance with the present disclosure is shown. In some embodiments, the anchor 300 may include a root 305 having a first end 305a and a second end 305b opposite the first end 305a, wherein the root 305 has a diameter $d_{R1}$. For example, the root 305 may be a tube. A first bulb 310a may be disposed at the first end 305a and a second bulb 310b may be disposed at the second end 305b. The first and second bulbs 310a, 310b may be substantially circular in shape having a diameter d, e.g., a disk, although the bulbs may be any other shape, including but not limited to oval, elliptical, square, polygonal, and the like. The first and second bulbs 310a, 310b may have the same diameter, or may have different diameters. As described below, the diameter of the first and second bulb 310a, 310b should be large enough to spread the force of the anchor 300 to prevent it from tearing out of the annulus. The first and second bulbs 310a, 310b may have a thickness $t_a$ and $t_b$, where in some embodiments $t_a$ and $t_b$, may be equal to each other, and in other embodiments $t_a$ and $t_b$, may be different from each other. The thickness t may be thick enough to provide structural support to the first and second bulb 310a, 310b to prevent the anchor 300 from tearing out of the annulus. In some embodiments, bulb 310a, 310b may include a lip 325a, 325b (FIG. 3C).

The root 305 may connect at a center 315a, 315b of the respective bulb 310a, 310b, the root 305 being a tube and having a smaller outer diameter than an outer diameter d of the first and second bulbs 310a, 310b. In some embodiments, the root 305, first bulb 310a, and the second bulb 310b may be integrally formed, although in other embodiments the anchor 300 may be formed by coupling at least one of the root 305, the first bulb 310a, and the second bulb 310b together. In some embodiments, a weld 320a, 320b may be disposed at the center 315a, 315b of the bulb 310a, 310b at each end 305a, 305b of the root 305. In some embodiments, the weld 320a, 320b may be a gathering or termination of respective ends of the first bulb 310a and the second bulb 310b. The weld 320a, 320b may extend a length from the respective first or second end 305a, 305b of the root 305 in the center 315a, 315b of the bulb 310a, 310b. For example, the weld 320a, 320b may extend the same thickness t as the respective first or second bulb 310a, 310b, such that it does not extend beyond the lips 325a, 325b of the bulb 310a, 310b. In other embodiments, the weld 320a, 320b may be disposed outward from the bulb at the center 315a, 315b.

The anchor 300 may be formed of a flexible braided nitinol, to promote tissue growth in and around the anchors. In some embodiments, the anchor 300 may be electropolished. Promoting tissue growth may be advantageous as it may prevent the anchors from tearing out over time. Additionally, the annulus size may be fixed by the tissue growth. As will be described in detail below, the anchor 300 may be of a flexible material, e.g., a shape memory material, so that the anchor may be deliverable in a compressed or non-expanded state, and expanded or expandable or self-expanding to the formed shape described above. The components of the anchor 300, including but not limited to the root 305, the first bulb 310a, and the second bulb 310b, may be formed of the same braided nitinol material. For example, the first bulb 310a and the second bulb 310b may be braided in a manner differently than the root 305. The weld 320a, 320b may be formed of a metal material to provide structural support to the anchor 300. The weld 320a, 320b may be coupled to the anchor 300 by threading at least a portion of braided nitinol through an aperture of the weld 320a, 320b. The weld 320a, 320b may also be coupled to the anchor by adhesive or another bonding technique.

Additional exemplary embodiments of an anchor are illustrated in FIGS. 4A-4E. Anchor 400a shown in FIG. 4A may be similar to anchor 300 illustrated in FIGS. 3A-3C, including a root 405, a first bulb 410a disposed at a first end 405a of the root 405, and a second bulb 410b disposed at a second end 405b of the root 405, and having a diameter $d_{R2}$. The first bulb 410a may have a first inward surface 475a, and the second bulb 410b may have a second inward surface 475b, so that the first and second inward surfaces 475a, 475b face each other. The first bulb 410a may have a diameter $d_a$ and a thickness $t_{aa}$, and the second bulb 410b may have a diameter $d_a$ and a thickness $t_{ab}$. For example, the diameters of the first and second bulbs 410a, 410b may be sized the same. The thicknesses of the first and second bulbs 410a, 410b may also be sized the same, although it is understood that the first and second bulbs 410a, 410b may have different thicknesses (e.g., $t_{ab}$ does not equal $t_{aa}$). The first and second bulbs 410a, 410b may have a diameter in the range of approximately 1 mm to 15 mm. The thicknesses $t_{aa}$, $t_a$b, of the first and/or second bulbs 410a, 410b may have a range of approximately 0.01 mm to approximately 10 mm. A weld 420a, 420b may be disposed at a respective center 415a, 415b of the bulb 410a, 410b, along a central horizontal axis 430. In contrast to anchor 300, the first and second bulbs 410a, 410b may include a first and second extended end 435a, 435b, extending outward and connected to the respective first and second weld 420a, 420b. For example, the braided nitinol may form an integral anchor 400 including a first extended end 435a, a first bulb 410a, a root 405, a second bulb 410b, and a second extended end 435b.

Figure 4A:
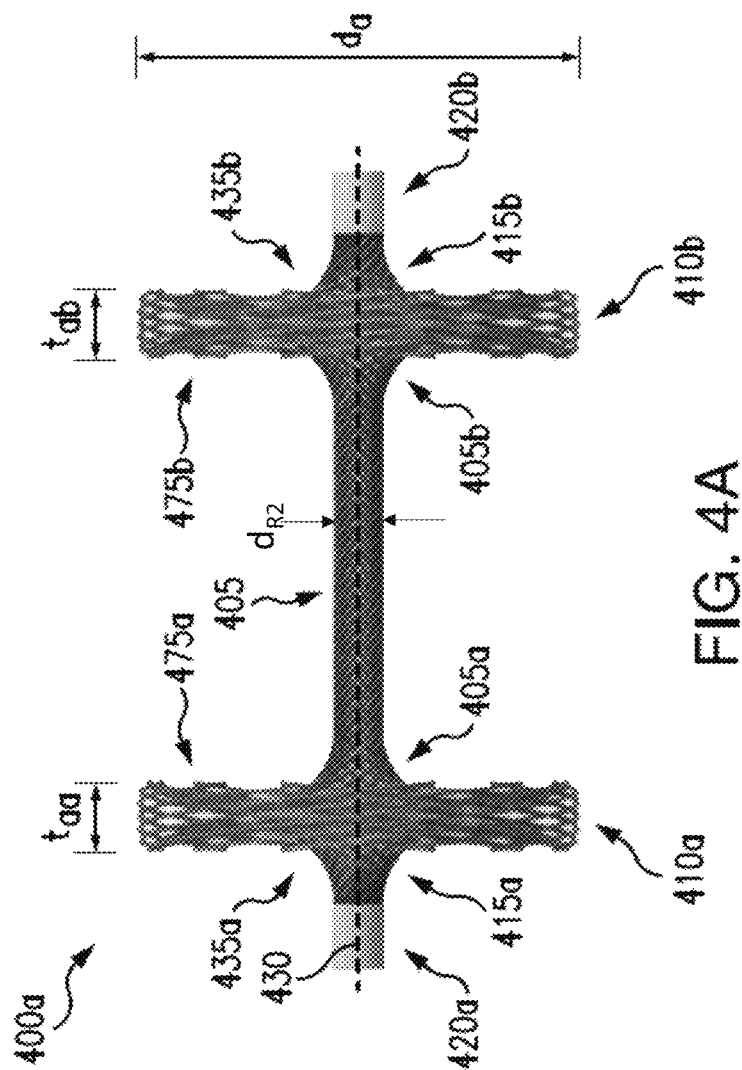
FIGS. 4A-4E illustrate exemplary embodiments of an anchor in accordance with the present disclosure.
Figure 4B:
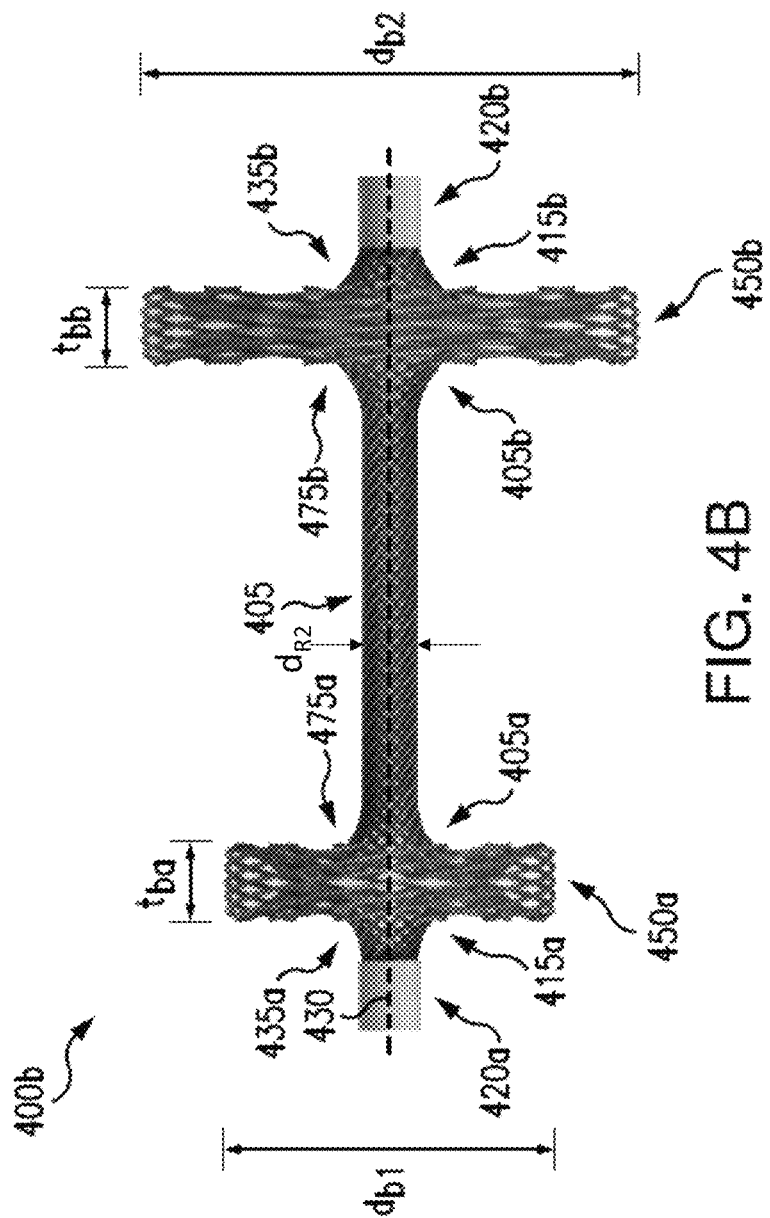

FIG. 4B illustrates an anchor 400b substantially similar to anchor 400a shown in FIG. 4A, except for the diameters of the first bulb 450a and the second bulb 450b. The first bulb 450a may have a first diameter $d_{db1}$, and the second bulb 450b may have a second diameter $d_{db2}$. In contrast to anchors 300, 400a, the first bulb 450a may be sized differently to have a different diameter from the second bulb 450b. As illustrated, the first diameter of the first bulb 450a may be smaller than the second diameter of the second bulb 450b, $d_{db1} < d_{db2}$, although it is understood that in other embodiments the first diameter may be larger than the second diameter, $d_{db2} < d_{db1}$. Different diameters may be advantageous in that larger diameters may distribute the stress of the plication across the surface area of the respective bulb, which may be beneficial for managing weaker areas of tissue and preventing tissue damage or tearing.

Figure 4C:
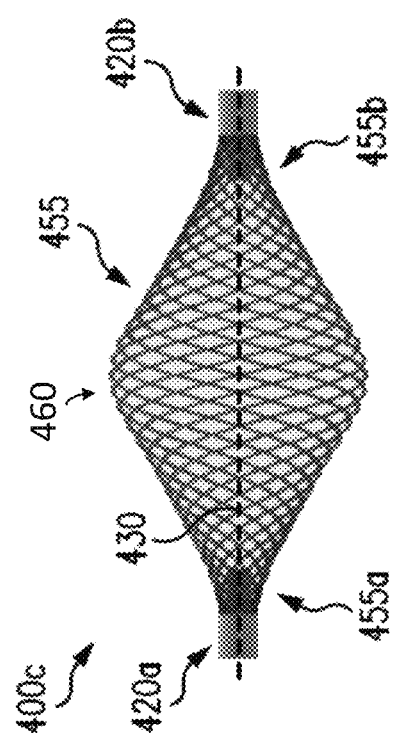

Anchor 400c illustrated in FIG. 4C may be a single bulb form 455 having a first end 455a and a second end 455b along central horizontal axis 430 and bounded by a first weld 420a and a second weld 420b. The single bulb form 455 may expand to a bulge 460 at a midpoint between the first end 455a and the second end 455b, which may expand to a diameter between 1 and 15 mm, or the single bulb form 455 may expand further to a bulb form similar to, e.g., one or other of the bulb forms on either end of the anchors depicted in FIGS. 4A-4B. In some embodiments, two anchors 400c may be connectable to each other along the central horizontal axis 430, e.g., via a suture or cable, to plicate the tissue. The suture or cable may be tightened, or pulled, to plicate the tissue and secure the tightened anchors 400c by a knot, crimp, or other securing fastener on the suture or cable.

Figure 4D:
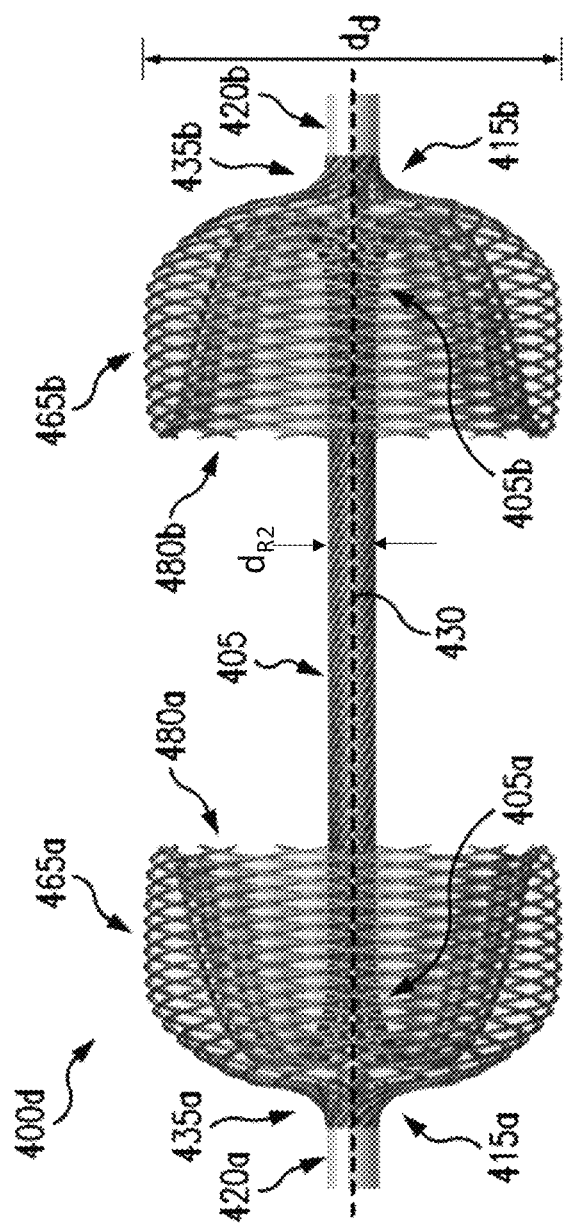

Anchor 400d illustrated in FIG. 4D may be similar to anchors 300 and 400a-400b, except instead of a first and second bulb formed at respective ends of the root, the anchor 400d may include a first umbrella, mushroom, or reverse concave end 465a and a second umbrella, mushroom, or reverse concave end 465b. For example, the first and second umbrella ends 465a, 465b may extend inward and away from the first and second welds 420a, 420b, over the respective first and second ends 405a, 405b, and a portion of the root 405, like an umbrella. A first and second bottom portion 480a, 480b may extend inward along central horizontal axis 430, and may be configured for displacement adjacent an annulus tissue (e.g., tissue surrounding a mitral or tricuspid valve). The first and second umbrella ends 465a, 465b may have a diameter $d_d$, and it is understood that the diameter of the first umbrella end 465a may be the same as or different from the second umbrella end 465b. Umbrella ends 465a, 465b may be advantageous in that they may be easily compressible in the delivery catheter described below, and self-expandable upon insertion into the annulus.

Figure 4E:
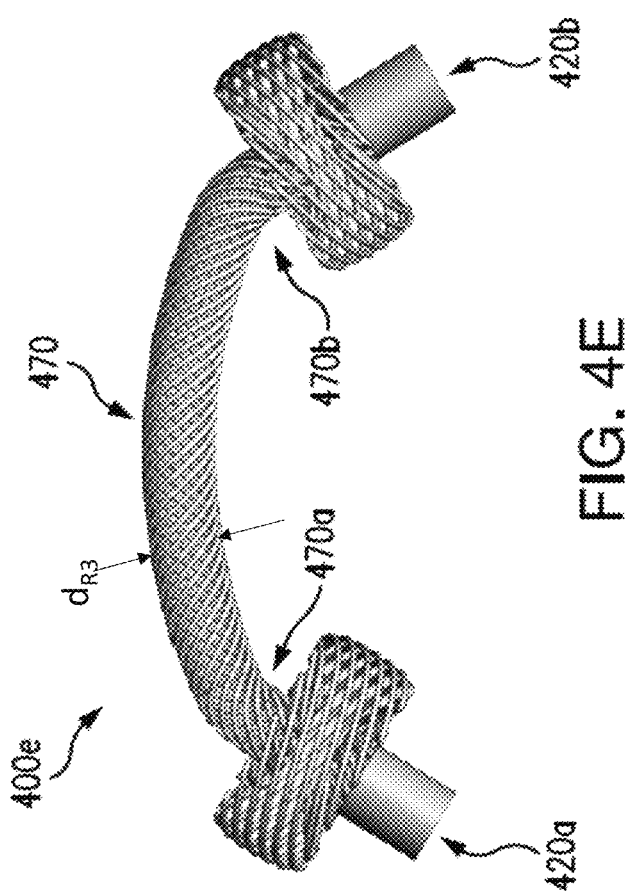

FIG. 4E illustrates anchor 400e, having a curved root 470, a first end 470a, and a second end 470b, and having a diameter $d_{R3}$. A first bulb and a second bulb may be coupled to the respective first and second end 470a, 470b via first and second welds 420a, 420b, and may be any of bulbs 310a-310b, 410a-410b, 450a-450b, or umbrella ends 465a-465b. As described above, the anchors 300 and 400a-400e may be formed of a flexible material, e.g., braided nitinol material. For example, the anchors 300 and 400a-400e may be flexible to bend in a curve. However, it may be advantageous to form a root 470 having an initial curvature so that the anchor 400e has less elasticity to revert to an unbended shape. This may help prevent the anchor 400e from tearing out of the annulus once inserted, as will be described below.

In embodiments, such as the anchor configurations of FIGS. 3A-3C and 4A-4E, an opening may be provided through the length of the root, which communicates at each end of the root with openings which may be provided through the thickness of the bulbs, the openings together defining a through-lumen along the entire length of the anchor, in the compressed state or the expanded state, or both. The through-lumen may accommodate components associated with a delivery device for the anchor or delivery of the anchor, e.g., a suture, as described further below.

In embodiments, one or more anchors 300, 400a-400e may be implanted in mitral and/or tricuspid annular tissue, to reduce the diameter and support closure of the atrioventricular valve. Each implanted anchor may reduce the annular perimeter of the atrioventricular valve by up to 5 mm, which may follow a ratio of needle throw length in the annulus tissue to root length, e.g., a 2:1 ratio, although this may vary based on user preference. For example, needle throw lengths may be between 0 mm and 16 mm, or greater, and depths of approximately 1 mm to 4 mm, and may be variable based on the medical professional controlling the needle, by entry and exit points of the throw and depth of penetration of the needle.

Referring now to FIGS. 5A, 5B, an exemplary embodiment of a system 500 for implanting an anchor in accordance with the present disclosure is shown. A suture 505 may be thread through an anchor delivery device, e.g., a sheath 510, for at least partially housing an anchor 300, 400a-400e. The sheath 510 may be a hollow tube 515 extending along a longitudinal axis 520 and having a first end 515a and a second end 515b. At the first end 515a, the sheath 510 may include a tip 525 attached to the hollow tube 515. In some embodiments, the tip 525 may be formed integrally with the hollow tube 515 and in other embodiments, the tip 525 may be coupled to the hollow tube 515 by known means, e.g., threads, screws, solder, adhesive, welding, and the like. The tip 525 may be conical in shape, e.g., to provide a dilating effect for ease in threading through annulus tissue. In embodiments, the tip 525 may be formed of metal, and may be clamped by a user during use to move the sheath 510, thereby exposing an anchor 300, 400a-400e. An opening 540 may be disposed at an end 535 of the tip 525, so that the suture 505 may extend out of the tip 525, and the sheath 510 may be slidable with respect to the suture 505 along the longitudinal axis 520. In embodiments, the sheath 510 may be movable by the medical professional during use, for example, via forceps (see e.g., FIGS. 7C-7D).

The second end 515b of the hollow tube 515 may be open, e.g., so the anchor 300, 400a-400e may be unsheathed at the second end 515b, as the sheath 510 and suture 505 are slid with respect to each other along the longitudinal axis 520. The hollow tube 515 may at least partially house an anchor 300, 400a-400e, with the suture 505 extending through the first bulb, root, and second bulb, of the anchor 300, 400a-400e. The suture 505 may be tied at either or both ends of the anchor to fix the anchor relative to the suture 505, e.g., by knots 530 or other known fixing means, including but not limited to mechanical fasteners, adhesive, and the like. In some embodiments, an anchor 300, 400a-400e may be fully housed within the hollow tube 515, with the respective first and second bulbs in a collapsed form. As described above, the anchor 300, 400a-400e may be made of a flexible material and may be configured to self-expand when unsheathed (e.g., formed of a shape memory material, such as nitinol).

Figure 7A:
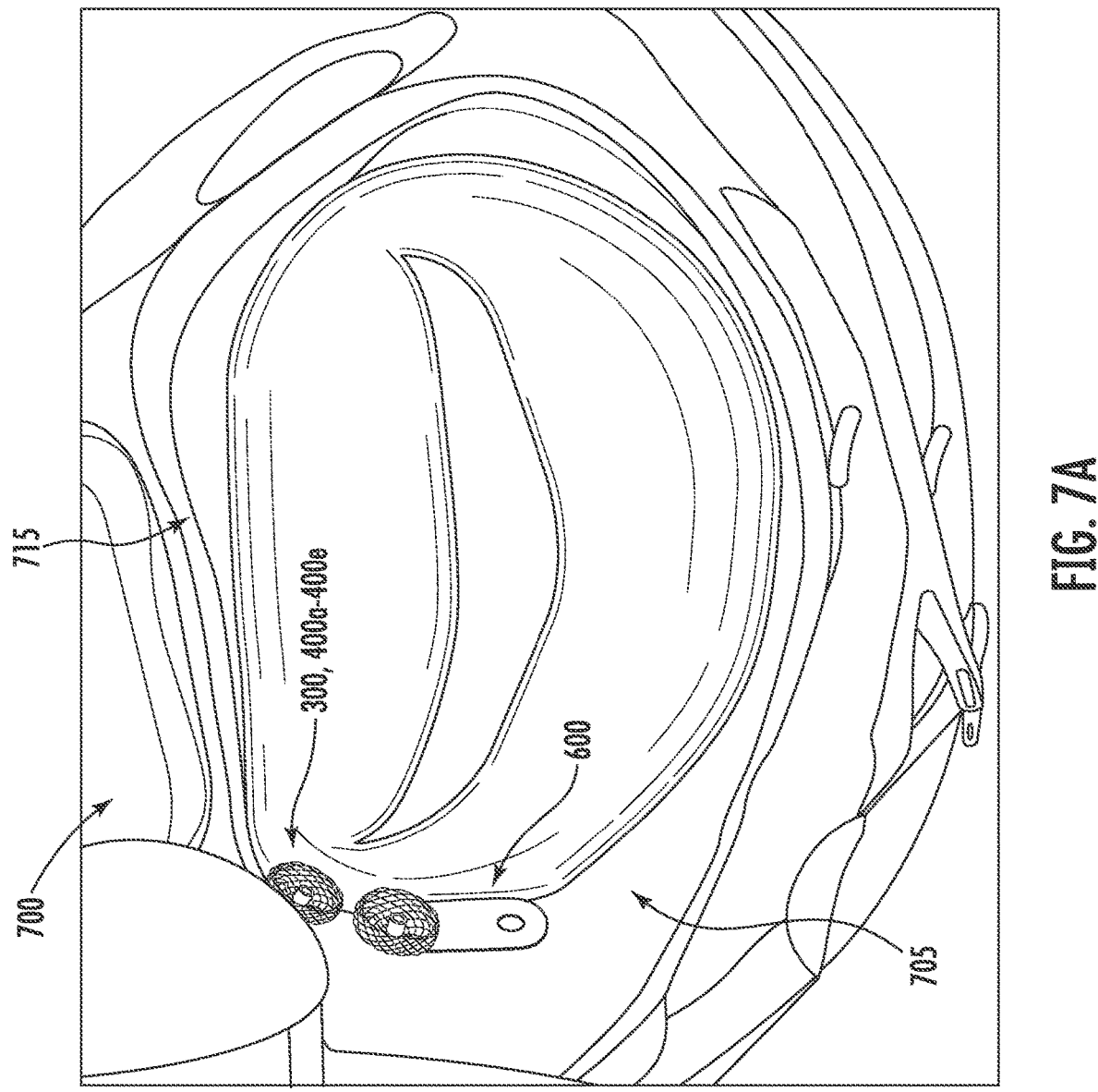
FIGS. 7A-7E illustrate an exemplary embodiment of an anchor delivery method for an atrioventricular valve in accordance with the present disclosure.
Figure 7B:
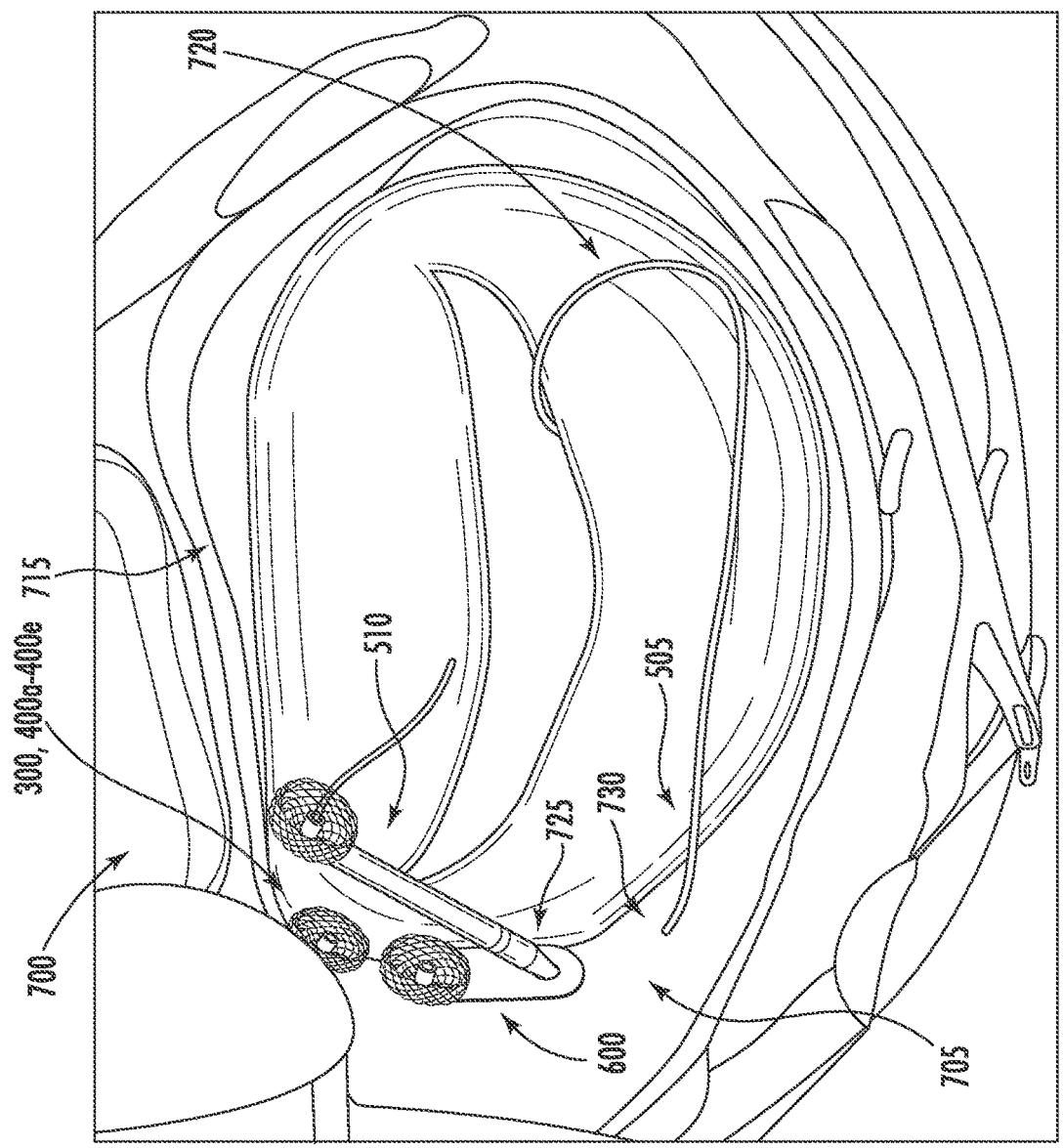

A needle 720 may be coupled to an end of the suture 505 for piercing the annulus tissue for anchor placement (see FIG. 7B). In embodiments, the needle 720 may be operable by the medical professional, e.g., during surgery, via a needle driver (not shown). For example, a path of the needle 720 may be manually prescribed by the medical professional performing the plication in open access surgery or ported surgery. In some embodiments, the needle 720 may be controllable by a robotic needle driver, driven by the medical professional during ported surgery. As the suture 505 is drawn through the tissue, the sheath 510 and at least a portion of the anchor 300, 400a-400e may be threaded through the annulus tissue. In some embodiments, a first or second bulb 310a-310b, 410a-410b, 450a-450b, or umbrella ends 465a-465b may be unsheathed, so that when the sheath enters the annulus tissue, a first or second bulb 310a-310b, 410a-410b, 450a-450b, or umbrella ends 465a-465b, may remain exposed while the other of the first or second bulb 310a-310b, 410a-410b, 450a-450b, or umbrella ends 465a-465b, may be threaded through the tissue, e.g., along the path of the needle, anchoring in the annulus tissue.

In some embodiments, a connector, or pledget 600, as shown in FIG. 6 may be included on the suture 505 with the anchor 300, 400a-400e, for placement on the annulus tissue. It may be advantageous to include a pledget to prevent an anchor 300, 400a-400e from tearing out of the annulus tissue. Although a pledget 600 is shown and described, it is understood that any connecting member may be used to link anchors together in the annulus tissue. For example, in some patients at an advanced stage of disease having a damaged atrioventricular valve, the surrounding tissue may not be strong enough to hold the anchor alone. The pledget 600 may spread the forces over a larger surface area of the annulus tissue, reducing potential for tearing. Additionally, the pledget 600 may provide axial strength to prevent the atrioventricular valve from stretching out over time, allowing the valve to open. This may be advantageous to prevent additional procedures for a patient over time. The pledget 600 may be a substantially flat disk 605 (see FIGS. 6, 7C), having a first opening 610a and a second opening 610b, for receiving a root 305, 405, 470 of an anchor 300, 400a-400e. In some embodiments, the thickness of the flat disk 605 may be approximately 0.005"-0.007". The first and second openings 610a, 610b may be large enough to receive the root 305, 405, 470 of the anchor 300, 400a-400e (e.g., at least 1 mm), but smaller than a diameter of the first and second bulbs 310a-310b, 410a-410b, 450a-450b, or umbrella ends 465a-465b (e.g., smaller than 5 mm, 7 mm, 10 mm, depending on bulb diameter for the selected anchor 300, 400a-400e). In this manner, the openings 610a, 610b allow for the bulbs to self-expand and help to prevent the bulbs from pulling out of the annulus tissue. The inward surfaces (e.g., 475a, 475b in FIGS. 4A-4B) of adjacent bulbs on neighboring anchors may contact respective openings of pledget 600 linking the anchors, and the pledget 600 may be disposed between the inward surfaces of the first and second bulbs 310a-310b, 410a-410b, 450a-450b and the annulus tissue. The anchor 300, 400a-400e may hold the annulus tissue in tension, including in a series of further adjacent anchors linked together by pledgets, thereby allowing at least a partial closure of the enlarged atrioventricular valve.

An exemplary embodiment of the pledget 600 may include the disk 605 having a first end 605a and a second end 605b and an extended body therebetween (see FIG. 6). In some embodiments, the first and second ends 605a, 605b may have a curvature, although the disk 605 may have any shape, e.g., circular, oval, square, etc., to allow for an anchor 300, 400a-400e to hold against the annulus tissue and to link efficiently with adjacent anchors. It may be advantageous for the pledget to have first and second ends 605a, 605b as curvatures, to reduce potential of emboli formation. The pledget 600 may be substantially flat so a surface of the pledget may contact the annulus tissue, thereby spreading out a force of the anchor 300, 400a-400e holding the annulus tissue in tension. As described above, this may be advantageous to reduce potential for tearing over a period of time, and may encourage tissue growth around the bulbs 310a-310b, 410a-410b, 450a-450b of the anchor 300, 400a-400e.

In some embodiments, the pledget 600 may be formed of a flexible material, e.g., the pledget 600 may be an electrospun fibrous pledget. In some embodiments, the pledget 600 may be formed of silicone, ChronoFlex®, and/or a combination of polymer and fiber materials.

As will be described below (FIGS. 7A-7E), a pledget may be implanted with an anchor 300, 400a-400e in the annulus tissue to reduce an enlarged atrioventricular valve. In embodiments, the pledget 600 may be disposed between the bulbs of the anchors 300, 400a-400e by slip fit to the root 305, 405, 470. In some embodiments, the pledget may be attachable to the anchor 300, 400a-400e, in a known manner, including but not limited to fasteners, suturing, or adhering by welding, bonding, melting, soldering, and the like. As shown in FIG. 6A, a pledget 600 may be placed on the annulus tissue may be collapsed within the sheath 510. A root 305, 405, 470 of a first anchor 300, 400a-400e may be positioned through one of the first opening or second opening 610a, 610b, with the disk 605 rolled up around the root 305, 405, 470 along the longitudinal axis 520. The other of the first or second opening 610a, 610b may be free from the root 305, 405, 470 of the first anchor 300, 400a, 400e, so that an adjacent anchor 300, 400a-400e (e.g., second, third, . . . n anchors for implantation) may be connected. In this manner, the pledget 600 may link a series of anchors 300, 400a-400e around the annulus tissue.

As the first anchor 300, 400a-400e is implanted, the pledget 600 may also be unsheathed, to unfurl after threading the delivery device through the annulus tissue and as the second bulb is expanded. In other embodiments, the pledget may be provided to the first anchor (e.g., as described below with adjacent anchors), after the delivery device is threaded through the annulus tissue and before the second bulb is expanded. Referring now to FIGS. 7A-7E, an exemplary embodiment of a method for implanting one or more anchors 300, 400a-400e in an atrioventricular valve 700 in accordance with the present disclosure is shown. Anchors 300, 400a-400e may be delivered to the annulus tissue surgically, for example, as described herein, and/or percutaneously, as described in co-pending application filed concurrently, entitled "Delivery and Occlusion Devices for Paravalvular Leak" (62/593,167), which is herein incorporated by reference in its entirety. For example, surgical delivery, e.g., open-heart surgery or open access surgery, and/or ported surgery, may use the sheath 510 for delivering the anchor 300, 400a-400e. The anchors 300, 400a-400e may be delivered percutaneously by a catheter, e.g., via femoral artery, jugular, or ported graft. In percutaneous embodiments (not shown), a camera may be connected to or associated with a catheter delivery system for a percutaneous delivery of the anchors, so that a user may verify a desired location of the annulus tissue 705 for placement of the anchor 300, 400a-400e and/or pledgets 600. FIG. 7A illustrates a first anchor 300, 400a-400e placed in annulus tissue 705, extending through a first or second opening 610a, 610b of a pledget 600. It may be advantageous to insert a first anchor 300, 400a-400e in the annulus 705 adjacent to the fibrous trigone area 715 (e.g., annulus tissue around the anterior leaflet), near an A1-P1 leaflet joining of the valve 700, e.g., where an anterior leaflet and a posterior leaflet are joined. Although the pledget 600 may be rotatable about the root 305, 405, 470 of the first anchor 300, 400a-400e, the pledget may be adjusted to extend from the first anchor 300, 400a-400e, adjacent the annulus tissue 705 around the atrioventricular valve 700. The other of the first or second opening 610a, 610b may therefore be accessible for a needle 720 to thread through, to pull another anchor through the annulus tissue 705.

Figure 7C:
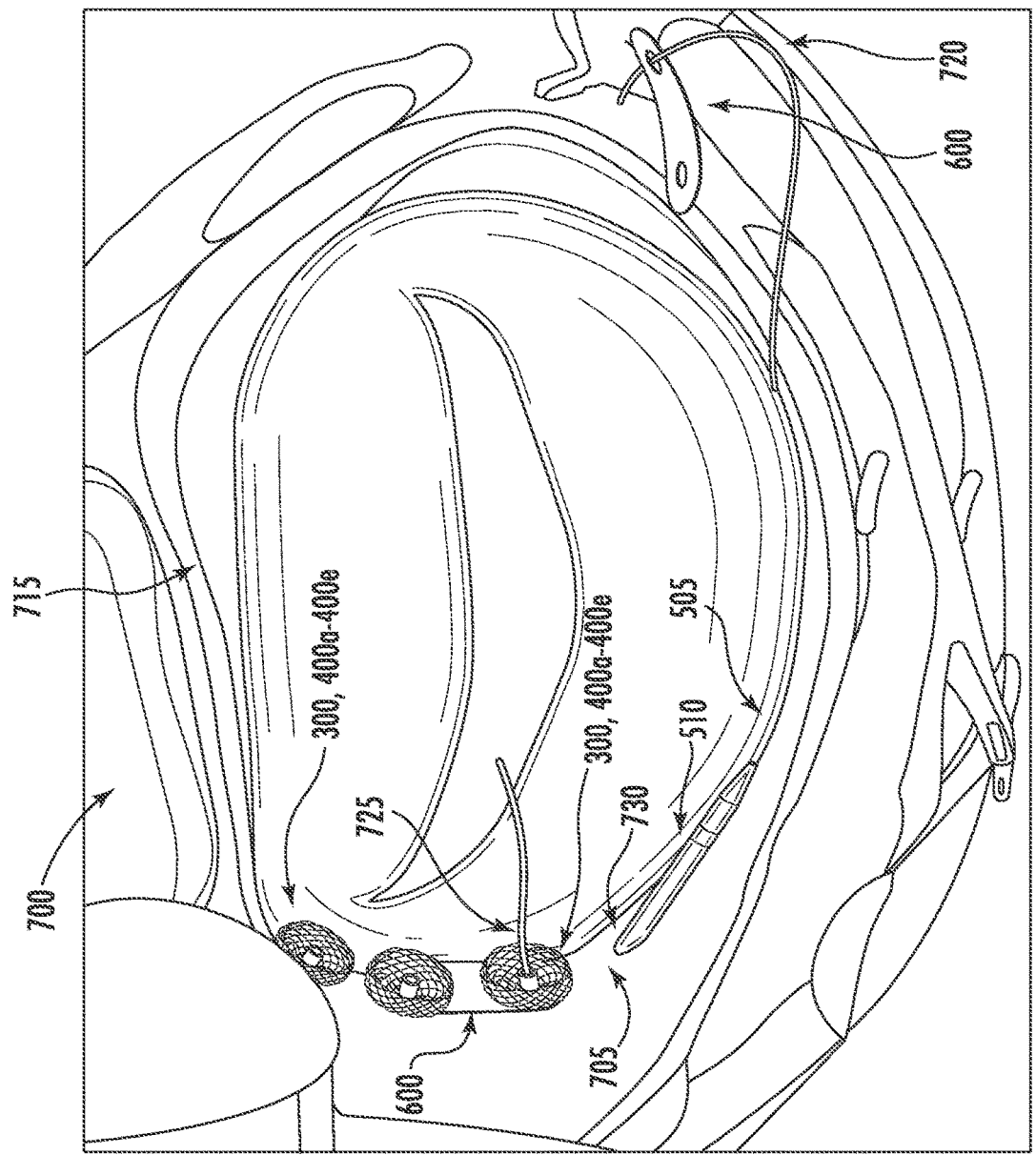

Referring now to FIG. 7B, a needle 720 for threading the suture 505 having an adjacent anchor 300, 400a-400e through the annulus tissue 705 is shown. As described above, the sheath 510 may at least partially house the adjacent anchor 300, 400a-400e, to thread through the annulus tissue 705. For example, a first or second bulb 310a-310b, 410a-410b, 450a-450b and at least a portion of the root 305, 405, 470, may be disposed within the sheath 510. The other of the first or second bulb 310a-310b, 410a-410b, 450a-450b, may remain exposed, to contact the annulus tissue 705 and/or the pledget 600. The needle 720, suture 505, and sheath 510 may pierce the annulus tissue 705 at a first area 725 and exit through a second area 730, on the annulus tissue 705 around the atrioventricular valve 700. The first area 725 may be an area of annulus tissue 705 through one of the first or second openings 610a, 610b, for threading the anchor 300, 400a-400e through the pledget 600. The second area 730 may be where the needle 720, suture 505, and sheath 510 exit the annulus tissue 705, as shown in FIG. 7C.

The needle and a length of the suture 505 may exit the annulus tissue 705 at the second area 730. A portion of the sheath 510 may exit the annulus tissue 705, e.g., the tip 525 at the first end 515a, with the second end 515b remaining in the annulus tissue 705, until a further pledget 600 is placed. FIG. 7C shows, for example, the suture 505 threaded through a first or second opening 610a, 610b of the further pledget 600 by the needle 720. The further pledget 600 may be adjusted along the suture 505 until placed on the annulus tissue 705, with the first end 515a of the sheath 510 extending through the first or second opening 610a, 610b.

Figure 7D:
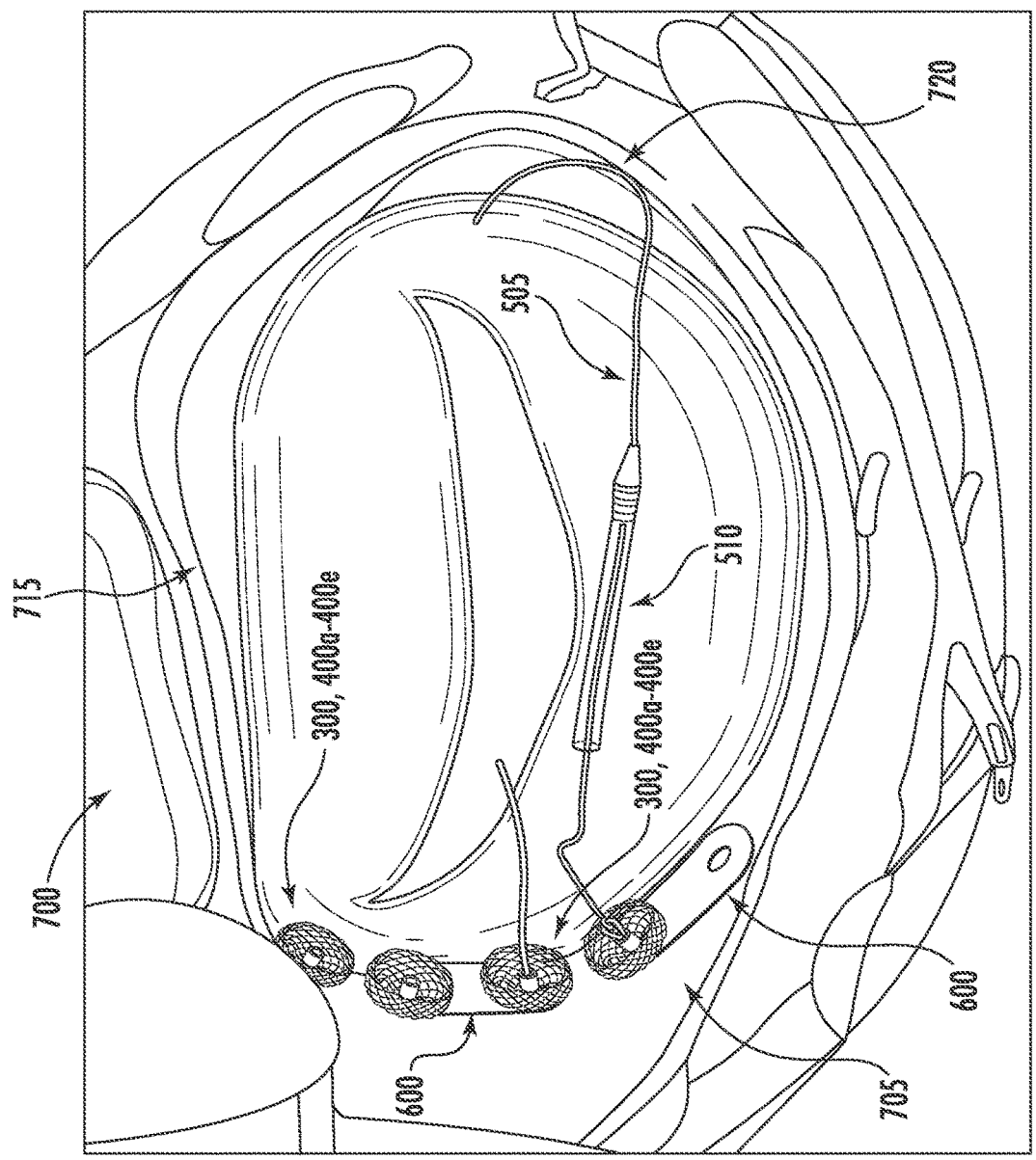

Once the further pledget 600 is adjusted to the desired position, e.g., contacting the annulus tissue 705 and extending outward for an additional anchor to be implanted through the other of the first or second opening 610a, 610b, the sheath may be pulled the rest of the way through the annulus tissue 705 to expose the other of the first or second bulb 310a-310b, 410a-410b, 450a-450b, as shown in FIG. 7D. As described above, the sheath 510 may be movable by the medical professional, e.g., surgeon, via forceps. In embodiments, the sheath 510 may be gripped, or clamped, at the first end 515a at the tip 525 and pulled away from the anchor 300, 400a-400e to expose the collapsed bulb 310a-310b, 410a-410b, 450a-450b. Once the other of the first or second bulb 310a-310b, 410a-410b, 450a-450b is exposed, it may expand to its full shape. In some embodiments, the bulb 310a-310b, 410a-410b, 450a-450b may self-expand, and in other embodiments, the bulb 310a-310b, 410a-410b, 450a-450b may be manually expanded by a user. The suture 505 may be trimmed, thereby separating the implanted anchor 300, 400a-400e from the needle 720 and sheath 510.

Figure 7E:
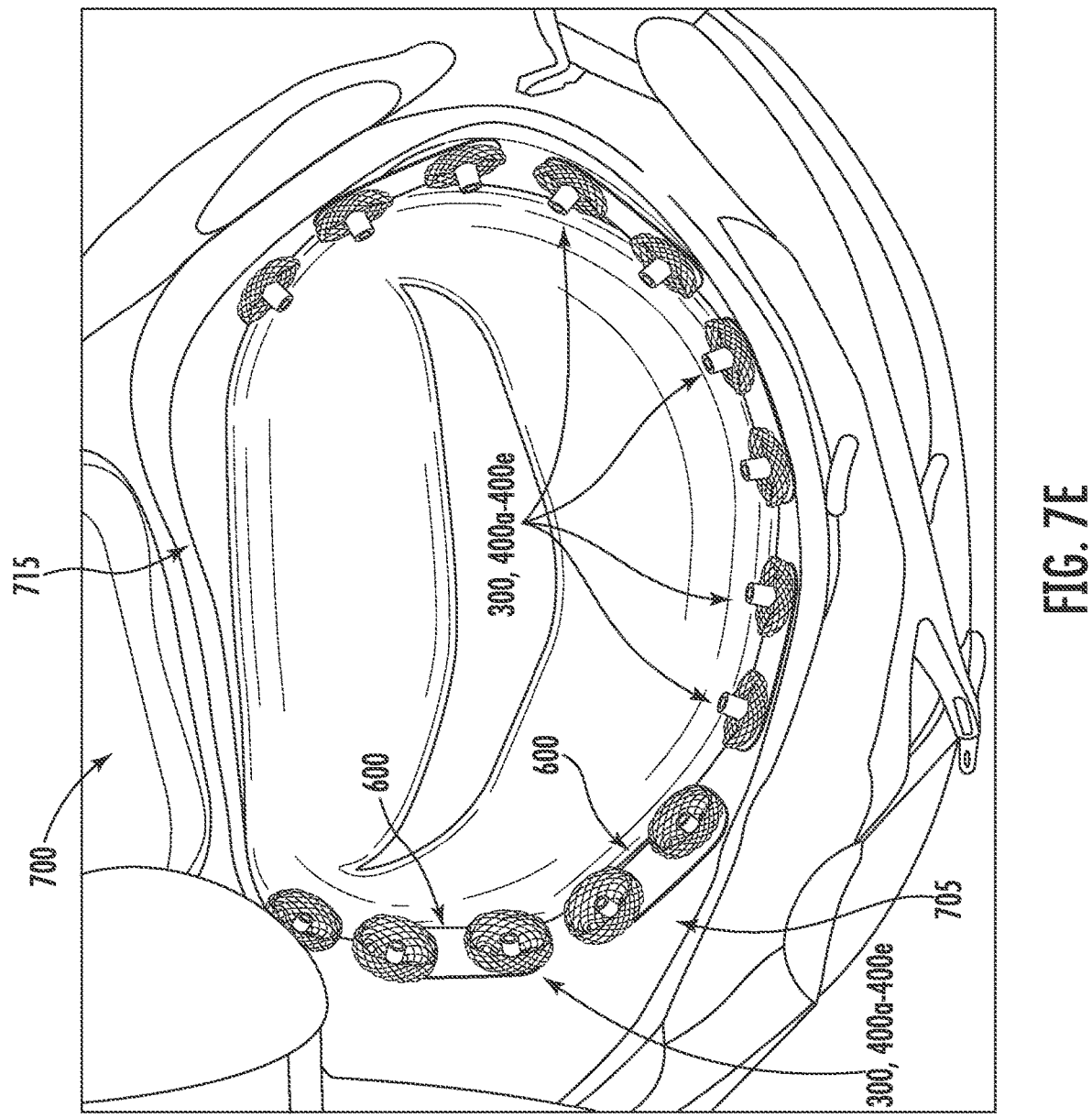

Additional anchors 300, 400a-400e and pledgets 600 may be implanted in a similar manner as described above with respect to FIGS. 7A-7D in the annulus tissue 705 around the atrioventricular valve 700 until the atrioventricular valve is closed, as shown in FIG. 7E. As described above, in some embodiments, anchors 300, 400a-400e may be disposed in the annulus tissue 705 around the atrioventricular valve except in the fibrous trigone area 715. Bulbs of the anchors 300, 400a-400e may be close together with each other, e.g., having spacing of approximately 1 mm to 5 mm. The fibrous trigone area 715 may not receive anchors due to the tissue wall. Although anchors 300, 400a-400e and pledgets 600 are shown in the rest of the annulus tissue 705, any amount of anchors 300, 400a-400e and/or pledgets 600 may be placed around the annulus tissue 705 for closing the atrioventricular valve 700. For example, in patients in a less advanced stage of disease, closure of the atrioventricular valve 700 may be accomplished by fewer anchors 300, 400a-400e and/or pledgets 600 strategically implanted around the annulus tissue 705. For example, anchors 300, 400a-400e may only be needed at the ends of the anterior and/or posterior leaflets.

Figure 8:
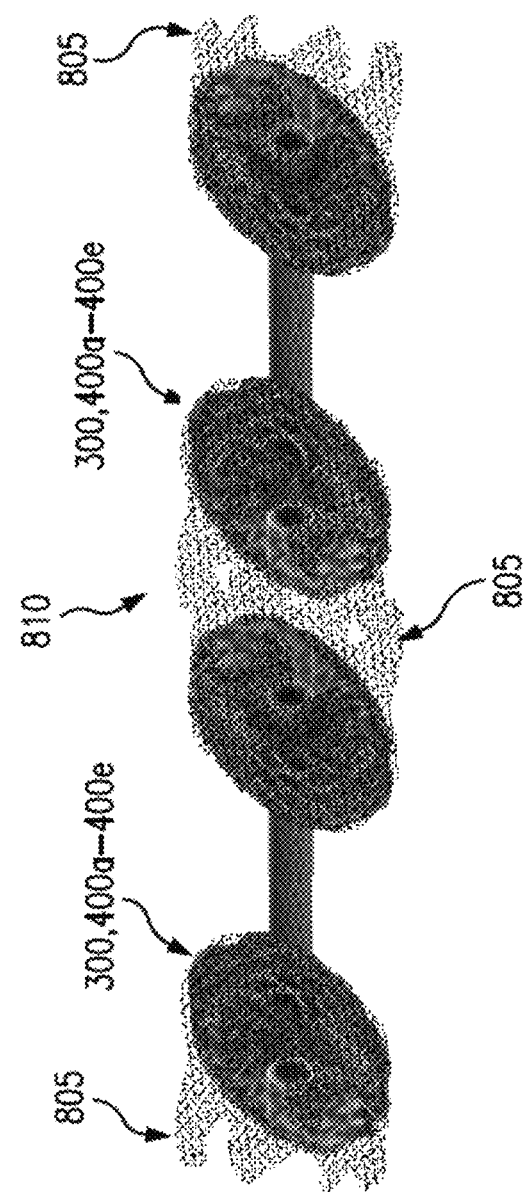
FIG. 8 illustrates an exemplary embodiment of a material interlocking anchors in accordance with the present disclosure.

The pledgets 600 may link each anchor 300, 400a-400e to adjacent anchors 300, 400a-400e, thereby standardizing distances between anchors around the annulus tissue 705 and promoting tissue growth to the anchors. In some embodiments, anchors 300, 400a-400e may be interlocked with each other by a connecting member, to promote tissue growth between the anchors. For example, anchor bulbs 310a-310b, 410a-410b, 450a-450b, or umbrella ends 465a-465b, may be coated in a material 805 as a connecting member, e.g., eSPIN nanofibers (electrospun fibrous material) as shown in FIG. 8. In some embodiments, the bulbs 310a-310b, 410a-410b, 450a-450b, or umbrella ends 465a-465b, may have the material 805 formed as a "skirt", e.g., an extra fold of the material 805 at least partially disposed on the bulb 310a-310b, 410a-410b, 450a-450b, or umbrella ends 465a-465b. For example, the material 805 may extend only on one side parallel to the respective root 305, 405, 470, or may extend 360° around the bulb 310a-310b, 410a-410b, 450a-450b, or umbrella ends 465a-465b. In some embodiments, the material 805 may be formed of a similar material used to form the pledget 600, although in other embodiments different materials are envisioned. For example, any rapid extrusion of nanofibers having a strength of 5-10 mils that are biocompatible to allow and/or promote tissue growth may be suitable for use. As shown in FIG. 8, two anchors 300, 400a-400e may be interlocked together, for example, indicated at reference numeral 810, by the material 805 extending from the respective bulbs 310a-310b, 410a-410b, 450a-450b, or umbrella ends 465a-465b. The material 805 may be pre-coated on the bulbs 310a-310b, 410a-410b, 450a-450b, or umbrella ends 465a-465b, with molded and/or electrospun material that may allow for tissue growth. As described above, since pledgets 600 with a uniform length may be used to standardize distances between anchors 300, 400a-400e when implanted in the annulus tissue 705, it may be determinable how much material 805 is needed to interlock the bulbs 310a-310b, 410a-410b, 450a-450b, or umbrella ends 465a-465b, from the respective anchors 300, 400a-400e together. The material 805 may be selected to be lubricious, and/or fiber-filled for inelastic properties, so that displacement of the material 805 during implantation is minimized and/or eliminated. For example, some embodiments may include an electrospun material having a thickness up to approximately 0.020 inches thick material or coating over the bulbs 310a-310b, 410a-410b, 450a-450b, or umbrella ends 465a-465b.

Figure 9:
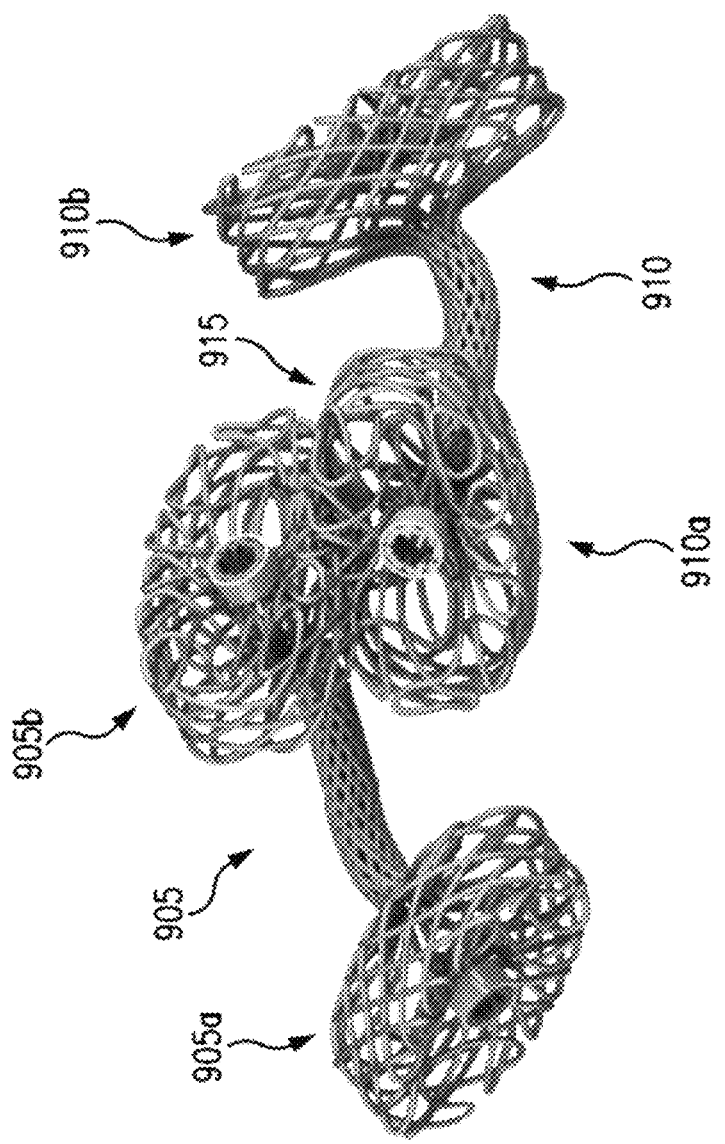
FIG. 9 illustrates an exemplary embodiment of interlocking anchors in accordance with the present disclosure.

Although the material 805 may be used to interlock anchors in the annulus tissue 705, in other embodiments, the anchors 300, 400a-400e may be interlocked together directly. As shown in FIG. 9, and described above, although the bulbs 310a-310b, 410a-410b, 450a-450b, or umbrella ends 465a-465b may be circular, the bulbs may form another shape, e.g., elliptical. An elliptical shape may be advantageous to increase surface area of bulb-to-bulb contact between anchors. In some embodiments, a first or second bulb 310a-310b, 410a-410b, 450a-450b, or umbrella ends 465a-465b of an anchor 300, 400a-400e may be circular, and the other of the first or second bulb 310a-310b, 410a-410b, 450a-450b, or umbrella ends 465a-465b may be elliptical. In some embodiments, both bulbs may be elliptical for interlocking several anchors in series with each other. For example, FIG. 9 illustrates a first anchor 905 interlocked with a second anchor 910. The first anchor 905 may have a first bulb 905a and a second bulb 905b, and the second anchor 910 may have a first bulb 910a and a second bulb 910b. The second bulb 905b of the first anchor 905 may be interlocked with the first bulb 910a of the second anchor 910. In embodiments, this may be accomplished during implantation. For example, the needle 720 may pierce the annulus tissue 705 through the anchor bulb to be interlocked. Thus, if a user desires to interlock the second anchor 910 after the first anchor 905 has been implanted, the needle, or pincer arms of a catheter delivery device, or mechanism of another delivery device, may be thread through the second bulb 905b of the first anchor 905. When the first bulb 910a of the second anchor 910 is deployed, or expanded, it may interlock with the second bulb 905a of the first anchor 905, indicated at reference numeral 915. In embodiments having interlocked bulbs between the first and second anchors 905, 910, pledgets (see FIG. 6) may be used as well. In some embodiments the pledget 600 may have first and second openings 610a, 610b, spaced closer together so that the respective bulbs of the first and second anchors 905, 910 may interlock.

Figure 10A:
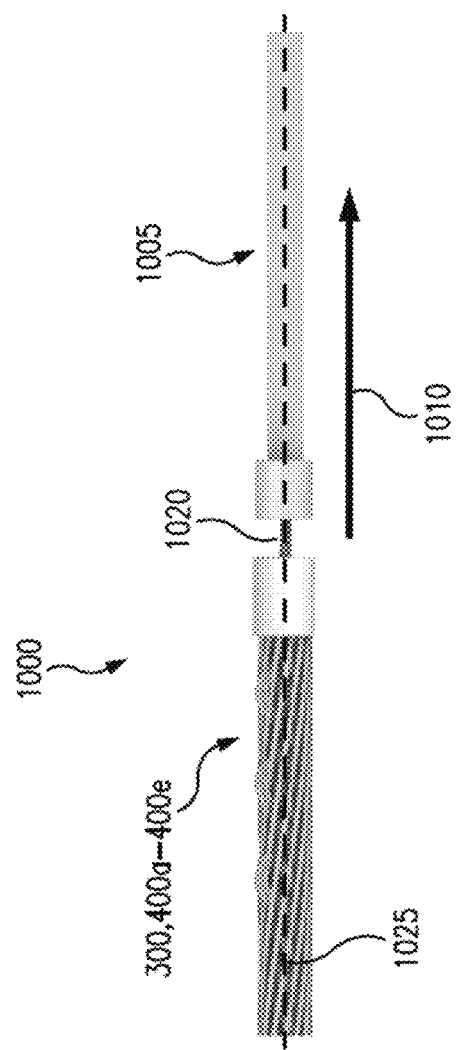
FIGS. 10A-10B illustrate an exemplary embodiment of an internal anchor release mechanism in accordance with the present disclosure.
Figure 10B:
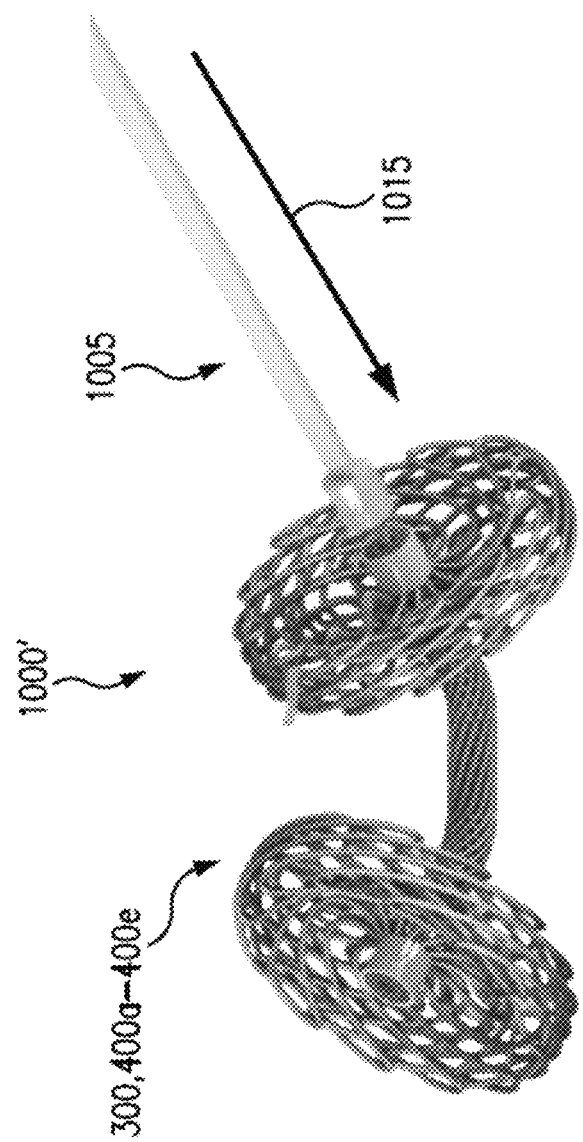

As described above, some anchors 300, 400a-400e may be configured for controlled expansion. Referring now to FIGS. 10A-10B, an internal anchor release system 1000, 1000' and method in accordance with the present disclosure is shown. In some embodiments, an anchor 300, 400a-400e may be disposed within the sheath 510, or catheter, in a collapsed form for deployment. For example, the self-expanding bulb 310a-310b, 410a-410b, 450a-450b, or umbrella ends 465a-465b, may be collapsed to the diameter $d_{R1}$, $d_{R2}$, $d_{R3}$ of the respective root 305, 405, 470. In embodiments, a pledget 600 may also be deliverable with the anchor 300, 400a-400e, disposed on the root 305, 405, 470 between the bulbs 310a-310b, 410a-410b, 450a-450b, or umbrella ends 465a-465b, of the anchor 300, 400a-400e. A stylet 1005 may be removably attachable to and slidable with a suture 1020, which may be connected internal to the anchor 300, 400a-400e. For example, the suture 1020 may be woven through the first or second bulb 310a-310b, 410a-410b, 450a-450b, or umbrella ends 465a-465b, internal to the anchor 300, 400a-400e. The stylet 1005 may be used for towing, or pulling the anchor 300, 400a-400e along a longitudinal axis 1025 in a direction indicated by arrow 1010. For example, towing, or pulling, the anchor 300, 400a-400e by the stylet 1005 may lock the anchor 300, 400a-400e in tension, so that as the anchor 300, 400a-400e is removed from the sheath 510, or catheter, the anchor 300, 400a-400e may remain in an elongated state. In some embodiments, the stylet 1005 may attach to the anchor 300, 400a-400e by looping the suture 1020 through at least a portion of the anchor 300, 400a-400e. In some embodiments, when the anchor 300, 400a-400e is held in tension, the first or second bulb 310a-310b, 410a-410b, 450a-450b, or umbrella ends 465a-465b may be held in a collapsed state, to be a diameter similar to the diameter $d_{R1}$, $d_{R2}$, $d_{R3}$ of the respective root 305, 405, 470, and self-expand when deployed.

When the anchor 300, 400a-400e is placed in a desired location, e.g., in the desired location of the annulus tissue 705, the stylet 1005 may stop being pulled to hold the anchor 300, 400a-400e in tension. In some embodiments, the stylet 1005 may be pushed in a direction opposite of arrow 1010, e.g., indicated by arrow 1015. Pushing the stylet 1005 toward the anchor 300, 400a-400e may result in pushing the bulbs 310a-310b, 410a-410b, 450a-450b, or umbrella ends 465a-465b, in an expanded shape, or allow the bulbs to self-expand, indicated by reference numeral 1000'. For example, as the root 305, 405, 470 is no longer held in tension, the nitinol braiding of the root 305, 405, 470 may allow for gaps so that the braiding of the bulbs 310a-310b, 410a-410b, 450a-450b, or umbrella ends 465a-465b, may expand through the gaps of the root 305, 405, 470. The stylet 1005 may be separated from the anchor 300, 400a-400e by removal of the looping of the suture 1020 through the anchor 300, 400a-400e.

Figure 11C:
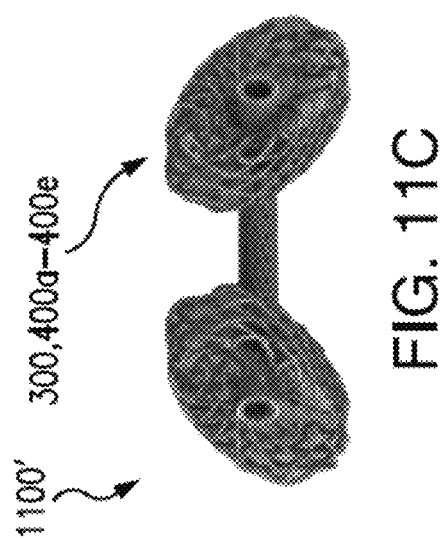
FIGS. 11A-11C illustrate an exemplary embodiment of an external anchor release mechanism in accordance with the present disclosure.
Figure 11A:
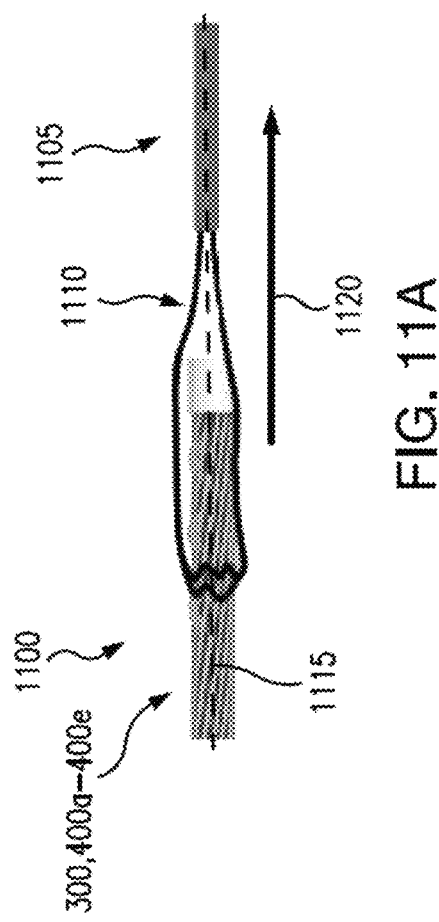
Figure 11B:
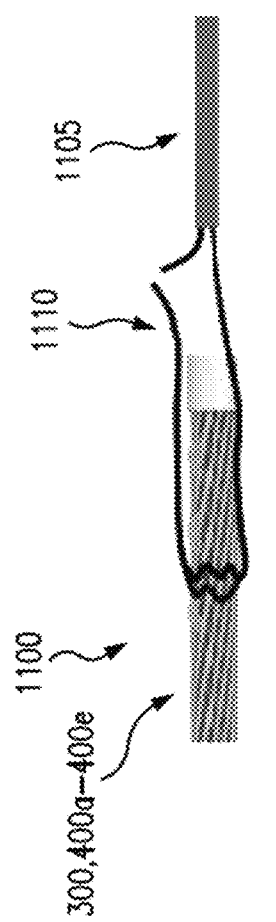

Referring now to FIGS. 11A-11C, an external anchor release system 1100, 1100' and method in accordance with the present disclosure is shown. A stylet 1105 may be connected to a suture 1110 that is removably attachable to an anchor 300, 400a-400e, for towing, or pulling, through a sheath 510 or catheter. The suture 1110 may be woven through at least a portion of the anchor 300, 400a-400e. The stylet 1105 may pull the anchor 300, 400a-400e via the suture 1110 in a direction indicated at arrow 1120 along longitudinal axis 1115. When the anchor 300, 400a-400e is towed, or pulled, the anchor 300, 400a-400e may be held in tension in a collapsed form. This may allow the anchor 300, 400a-400e to be pulled through a catheter lumen, or other catheter or sheath for placement in the annulus tissue and deployment.

When the anchor 300, 400a-400e is positioned in the desired location in the annulus tissue, the suture 1110 may be cut, or otherwise severed, and removed from the anchor 300, 400a-400e by pulling on the stylet 1105. Once the suture 1110 is removed from the anchor 300, 400a-400e, the anchor 300, 400a-400e may expand, e.g., the first and second bulbs 310a-310b, 410a-410b, 450a-450b, or umbrella ends 465a-465b may expand to their full shape to anchor the annulus tissue, as shown at reference numeral 1100' in FIG. 11C. In embodiments, a pledget 600 may also be deliverable with the anchor 300, 400a-400e, disposed on the root 305, 405, 470 between the bulbs 310a-310b, 410a-410b, 450a-450b, or umbrella ends 465a-465b, of the anchor 300, 400a-400e.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An anchor delivery system for repairing an atrioventricular valve, the anchor delivery system comprising:
   at least one elongate anchor having a first bulb on a first end and a second bulb on a second end; and
   an anchor delivery device including a sheath at least partially retaining the at least one elongate anchor in a collapsed form, wherein the anchor delivery device is configured to deliver the at least one elongate anchor to the atrioventricular valve;
   wherein the at least one elongate anchor is connectable in an expanded form to an adjacent anchor having a first bulb on a first end and a second bulb on a second end, a bulb of the at least one elongate anchor and a bulb of the adjacent anchor being configured to directly interlock together to link a series of anchors implanted at least partially around the atrioventricular valve.

2. The anchor delivery system according to claim 1, wherein the at least one elongate anchor is attached to a suture, the suture extending through the anchor delivery device for delivery through annulus tissue of the atrioventricular valve.

3. The anchor delivery system according to claim 2, wherein a needle is configured to pierce the annulus tissue, the needle being attached to the suture to pull at least the anchor delivery device or the at least one elongate anchor, or both, through the annulus tissue of the atrioventricular valve.

4. The anchor delivery system according to claim 1, wherein a bulb of the at least one elongate anchor is connectable to an adjacent anchor by a connecting member.

5. The anchor delivery system according to claim 4, wherein the connecting member is a pledget, such that the at least one elongate anchor is extendable through a first opening of the pledget and the adjacent anchor is extendable through a second opening of the pledget.

6. The anchor delivery system according to claim 4, wherein the connecting member is a material disposable on the bulbs of the at least one elongate anchor such that the material interlocks the bulb of the at least one elongate anchor and the adjacent anchor.

7. The anchor delivery system according to claim 4, wherein the connecting member is formed of an electrospun nanofiber material.

8. The anchor delivery system according to claim 1, wherein the at least one elongate anchor and an adjacent anchor are connectable to promote tissue growth.

9. The anchor delivery system according to claim 1, wherein the bulbs on the at least one elongate anchor are an elliptical shape.

10. The anchor delivery system according to claim 1, wherein the first bulb and the second bulb of the at least one elongate anchor are in a collapsed form when the at least one elongate anchor is retained in the sheath, and are expandable into an expanded form after deployment of the at least one elongate anchor in annulus tissue of the atrioventricular valve.

11. The anchor delivery system according to claim 2, wherein the suture is internal to the at least one elongate anchor, such that as the suture is pulled the at least one elongate anchor is held in tension in the collapsed form.

12. The anchor delivery system according to claim 2, wherein the suture is looped externally through the at least one elongate anchor, such that as the suture is pulled the at least one elongate anchor is held in tension in the collapsed form.

13. The anchor delivery system according to claim 1, wherein the at least one elongate anchor and an adjacent anchor are configured to be directly interlocked by threading at least a portion of the anchor delivery device through the bulb of the at least one elongate anchor, such that the adjacent anchor is interlocked with the at least one elongate anchor when deployed.

14. The anchor delivery system according to claim 5, wherein the pledget is configured to collapse within the anchor delivery device, such that for delivering the at least one elongate anchor to annulus tissue, the pledget is deployable for connecting the at least one elongate anchor to an adjacent anchor.

15. A method for repairing an atrioventricular valve, the method comprising:
  (a) piercing an annulus tissue at a first location by a needle to thread a suture through the annulus tissue to a second location along the annulus tissue, wherein the suture extends through an anchor delivery device at least partially housing a first anchor having a first end with a first bulb and a second end with a second bulb, the first anchor being connected to the suture for threading through the annulus tissue such that the first bulb of the first anchor is deployed at the first location of the annulus tissue;
  (b) extending the anchor delivery device at least partially through the second location of the annulus tissue;
  (c) deploying the second bulb of the first anchor at the second location along the annulus tissue by deploying the anchor from the anchor delivery device, wherein the first anchor contacts the annulus tissue;
  implanting a second anchor according to steps (a)-(c); and
  connecting the first anchor and the second anchor along the annulus tissue.

16. The method according to claim 15, wherein the first anchor and the second anchor are connected by a connecting member.

17. The method according to claim 16, wherein the connecting member is a pledget.

18. The method according to claim 16, wherein the connecting member is a material disposed on the first bulb and the second bulb of the first and second anchors.

19. The method according to claim 15, wherein the first or second bulb of the first anchor is connected to the first or second bulb of the second anchor.

\* \* \* \* \*